United States Patent [19]
Tabor et al.

[11] Patent Number: 6,116,413
[45] Date of Patent: Sep. 12, 2000

[54] COATING FOR BIOELECTRICAL STIMULATION AND RECORDING ELECTRODES

[75] Inventors: Bruce Tabor, Marsfield; Paul Michael Carter, Carlingford; David Kerry Money, Pennant Hills, all of Australia

[73] Assignee: Cochlear Limited, Lane Cove, Australia

[21] Appl. No.: 09/012,541

[22] Filed: Jan. 23, 1998

[51] Int. Cl.[7] .................................................. B65D 85/20
[52] U.S. Cl. ........................................ 206/205; 206/7.22
[58] Field of Search ............................. 206/205, 207, 206/213.1, 701, 722, 724, 726

[56] References Cited

U.S. PATENT DOCUMENTS

| | | |
|---|---|---|
| 4,034,854 | 7/1977 | Bevilacqua ............................. 206/205 |
| 5,237,991 | 8/1993 | Baker, Jr. et al. . |
| 5,762,185 | 6/1998 | Dulger ................................... 206/207 |

*Primary Examiner*—Jacob K. Ackun
*Attorney, Agent, or Firm*—Gottlieb Rackman & Reisman PC

[57] ABSTRACT

A packaging system for a bioelectrical stimulating and recording electrode is provided. The system includes a semi-porous protective container in which the electrode is housed. A conductive biocompatible and bioresorbable liquid partially fills the container in order for the electrode housed therein to be coated by the liquid. While the preferred conductive liquid is glycerol, other liquids may be chosen for practicing the invention.

17 Claims, 1 Drawing Sheet

COATING FOR BIOELECTRICAL STIMULATION AND RECORDING ELECTRODES

BACKGROUND OF THE INVENTION

A. Field of Invention

This invention relates to packaging for a bioelectrical electrode array, which can be used for stimulation, recording, or both, and more specifically, to a packaging system which includes a conductive liquid for ensuring electrical contact with the electrode that is bathed in the liquid.

B. Description of the Prior Art

A cochlear device is generally understood to be some type of implantable hearing aid which helps a specific class of patients for which conventional hearing aids are inadequate. As is well known, a cochlear device includes an electrode array of one or more electrodes which must perform appropriately for the device to function.

Typically, the electrode or electrodes of a cochlear device may need to be remotely tested for open circuits after packaging. It is believed that one prior art packaging included a sealed compartment of saline solution. The sealed compartment, however, could only be ruptured once in order to enable electrical contact between electrodes, and thereby enable testing for open circuit electrodes. In particular, in such a package the water content would evaporate after the compartment is ruptured—the test is thus essentially a "once only" test for open circuits. In other words, it cannot be conducted both immediately alter packaging and immediately prior to implantation if the "elapsed" time were sufficient to allow water evaporation.

Additionally, prior art packaging is known which includes a coating material made of polyvinyl alcohol. The polyvinyl alcohol is used to protect the electrode material. However, polyvinyl alcohol is not conductive, making electrode testing even more difficult. Moreover, polyvinyl alcohol increases the stiffness of the electrode material and makes its insertion more difficult.

Accordingly, it would be desirable to provide a packaging system that overcomes the above disadvantages. Furthermore, multiple electrodes are used in other biomedical applications as well and it would be desirable to provide a packaging which could be used for these other types of electrodes as well.

SUMMARY OF THE INVENTION

Generally speaking, in accordance with the invention, a packaging system for a bioelectrical stimulating and recording electrode is provided. The system includes a semi-porous protective container in which the electrode is housed. A conductive biocompatible and bioresorbable liquid partially fills the container in order for the electrode housed therein to be coated by the liquid. While the preferred conductive liquid is glycerol, other liquids may be chosen for practicing the invention.

It is therefore an object of the invention to provide an improved packaging system for a bioelectrical stimulating and recording electrode array.

Still another object of the invention is to provide electrical contact between the electrodes of an array such that electrical contact will remain after a cochlear device has been packaged.

Yet a further object of the invention is to provide the ability to test the operability of an electrode of a cochlear device.

A further object of the invention is to provide a protective coating for a bioelectrical stimulating and recording electrode which prevents absorption of substances that reduce polarization performance.

Still other objects and advantages of the invention will in part be obvious, and will in part be apparent from the following description.

The invention accordingly comprises a product and system possessing the features, properties and relation of components which will be exemplified in the product and system hereinafter described, and the scope of the invention will be indicated in the claims.

BRIEF DESCRIPTION OF THE DRAWINGS

For a fuller understanding of the invention, reference is made to the following description, taken in connection with the accompanying drawings, in which.

DETAILED DESCRIPTION OF THE PREFERRED EMBODIMENT

Figure 1:
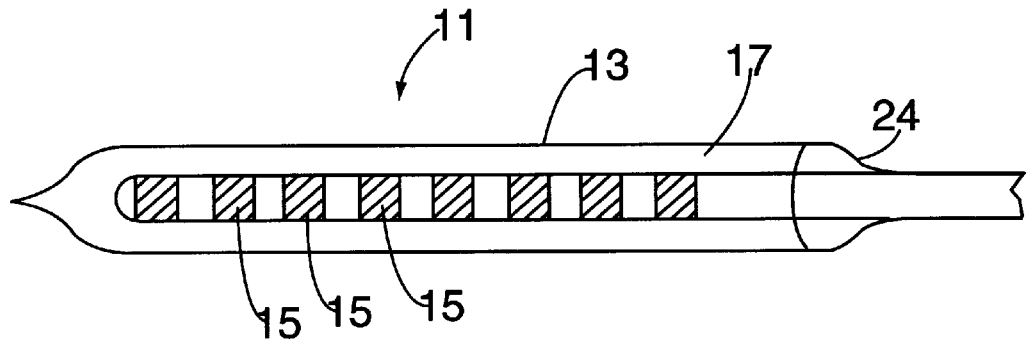
FIG. 1 is a cross-sectional view showing a bioelectrical stimulation and recording electrode contained in a packaging system made in accordance with the invention.

Referring first to FIG. 1, a packaging system generally indicated at 11 and made in accordance with the invention is now described. Packaging system 11 includes a semi-porous protective container 13 in which a bioelectrical stimulating and recording electrode 15 is housed. The container 13 may constitute the whole package or it may form a separate compartment within a larger package. Container 13 has a substantially tubular configuration and is made from silicone, or other similar material. Significantly, container or tube 13 is made of a material which is substantially permeable to a sterilizing media such as ETO/steam.

Packaging system 11 further includes a conductive biocompatible and bioresorbable liquid 17 for at least partially filling container 13. As can be appreciated, liquid 17 coats or otherwise bathes electrode array 15 as it is situated in container 13.

Liquid 17 should have a boiling point and vapor pressure at room temperature significantly greater than that of water. This prevents evaporation during storing of packaging system 11.

Liquid 17 is held in container or tube 13 by surface tension. However, preferably the liquid is held within the container by a seal 24 around the sleeve 23 which is impermeable to the liquid. Alternatively, a larger container may be used for housing the complete electrode assembly. Of most importance is for liquid 17 to be conductive so that electrode array 15 can be tested for open circuits after packaging within system 11 as described below. The preferred liquid 17 is saline-doped glycerol, i.e., a solution of 1% sodium chloride in glycerol, since it is substantially conductive and is more pliable than polyvinyl alcohol. Although saline-doped glycerol is the preferred liquid 17, other suitable high-boiling point biocompatible solvents include polyethylene glycol, propylene glycol, hyaluronic acid, and hydroxypropyl methylcellulose.

Alternatively, a liquid containing biocompatible salts, such as potassium chloride, sulfates, nitrites and phosphates, may be used.

As can be well appreciated, mixtures of more than one of these suitable liquids may be used, and some water may be added, or even small amounts of polyvinyl alcohol may be added.

The most important feature of the inventive system is that it enables remote testing of packaged bioelectrical stimulating and recording electrodes. This is because the liquid which bathes the electrodes in the packaging of the invention is both conductive and pliable.

Figure 2:
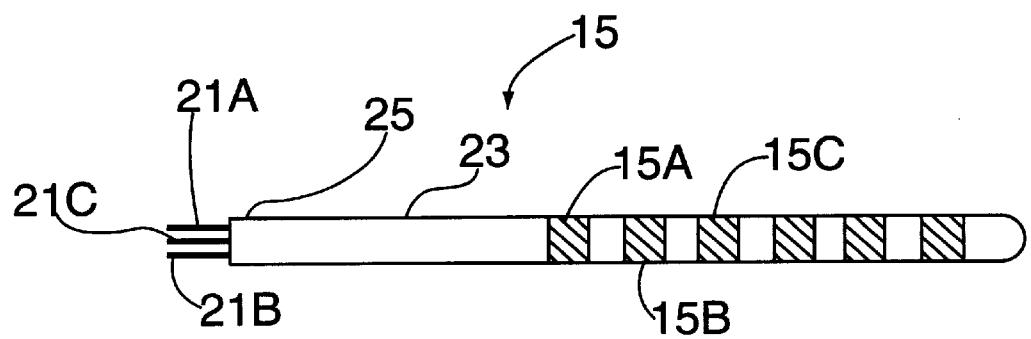
FIG. 2 shows an enlarged view of the electrode array.

Referring to FIG. 2, a typical array 15 includes a plurality of electrodes 15A, 15B, etc. disposed near a distal end. Each electrode is connected to a corresponding wire 21A, 21B, etc. extending through a sleeve 23 and being exposed at end 25.

Figure 3:
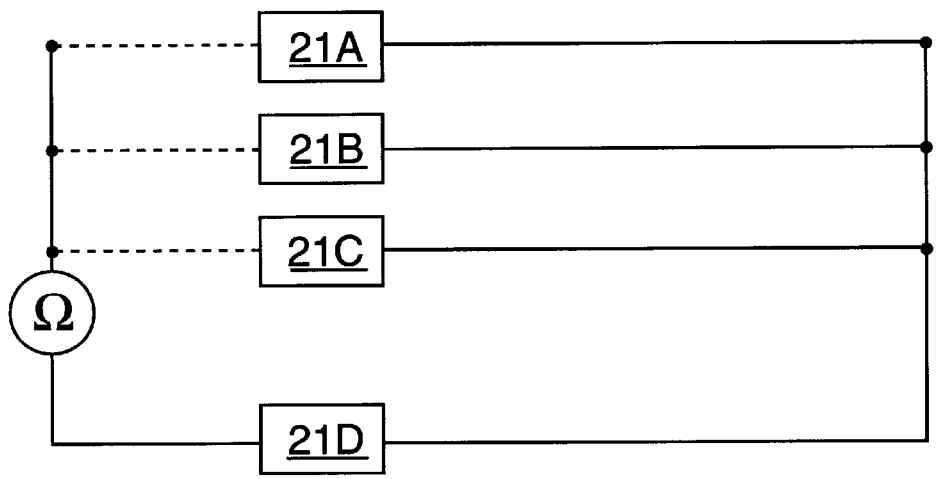
FIG. 3 is an electrical schematic view.

Since all the electrodes are bathed in the liquid 17, they are effectively shorted to each other. Therefore, the electrodes can be easily tested for continuity. For example, a shown in FIG. 3, each electrode and its conductor can be tested by checking the continuity between 21A, 21B . . . and 21D, which may be considered a common return.

If the array has only a single electrode, it may be tested by using liquid 17 for the return path.

It will thus be seen that the objects set forth above, among those made apparent from the preceding description, are efficiently obtained and, since certain changes may be made in the above system without departing from the spirit and scope of the invention, it is intended that all matter contained in this description and shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

I claim:

1. A packaging system for a bioelectrical stimulating and/or recording electrode array terminating in at least one electrode comprising:
    a protective container in which said electrode array is housed, said container being made of a material substantially permeable to a sterilizing material;
    a conductive biocompatible and bioresorbable liquid at least partially filling said container said electrode array being immersed in said liquid, said liquid being arranged and distributed within said container to enable the testing of said electrode array for open circuits without removing said electrode array from said packaging.

2. The system of claim 1, wherein said container is semiporous.

3. The system of claim 1 wherein said container is tubular in configuration.

4. The system of claim 1 wherein said container is a tear-away sheath.

5. The system of claim 1 wherein said liquid is a solution of a biocompatible salt in glycerol.

6. The system of claim 5, wherein said biocompatible salt is sodium chloride.

7. The system of claim 5 wherein said biocompatible salt is in proportion of approximately 1% by weight.

8. The system of claim 1 wherein the liquid is a solution of a biocompatible salt in a solvent selected from polyethylene glycol, propylene glycol, hyaluronic acid, and hydroxypropyl methylcellulose.

9. The system of claim 8, wherein said biocompatible salt is sodium chloride.

10. The system of claim 8 wherein said biocompatible salt is in proportion of approximately 1% by weight.

11. An electronic packaging system comprising:
    a housing made of a material substantially permeable to a sterilizing media;
    an electrode array extending into said housing and including at least two electrodes disposed in said housing and wires connected to said electrodes and extending outside said housing;
    a conductive liquid disposed in said housing with said electrodes being immersed in said liquid to allow said electrodes to be checked for continuity without removal from said container.

12. The system of claim 11 further comprising a seal for closing said housing.

13. The system of claim 11 wherein said housing is made of a material permeable to a sterilizing media.

14. The system of claim 11 wherein said liquid is a solution of a biocompatible salt in a solvent selected from polyethylene glycol, propylene glycol, hyaluronic acid, and hydroxypropyl methylcellulose.

15. A method for testing the electrical integrity of an implantable electrode array, including at least two electrodes each electrode with at least one lead connected thereto, comprising the steps of:
    a) housing the electrode bearing portion of said array in a protective container containing an electrically conductive liquid whereby said electrodes are in electrical contact with said liquid and said leads protrude from said container and whereby said liquid is substantially sealed within said container.
    b) for each electrode lead connecting a limited current source between said lead and one other lead;
    c) monitoring the flow of current between said current source and one of the leads in step b);
    d) on the basis of the monitoring in step c) either storing said container and electrode array of step a) until implantation of the array is required or discarding said array or unpackaging said array for implantation.

16. A packaging system for a bioelectrical stimulating and/or recording electrode array terminating in at least one electrode comprising:
    a protective container in which said electrode array is housed, said container being made of a tear-away sheath material;
    a conductive biocompatible and bioresorbable liquid at least partially filling said container said electrode array being immersed in said liquid, said liquid being arranged and distributed within said container to enable the testing of said electrode array for open circuits without removing said elctrode array from said packaging.

17. A packaging system for a bioelectrical stimulating and/or recording electrode array terminating in at least one electrode comprising:
    a protective container in which said electrode array is housed;
    a conductive biocompatible and bioresorbable liquid at least partially filling said container said electrode array being immersed in said liquid, said liquid being arranged and distributed within said container to enable the testing of said electrode array for open circuits without removing said electrode array from said packaging;
    wherein said conductive biocompatible and bioresorbable liquid has a boiling point significantly greater than that of water and a vapor pressure at storage temperature significantly less than water.

* * * * *